United States Patent [19]

Sussman et al.

[11] Patent Number: 5,236,827
[45] Date of Patent: Aug. 17, 1993

[54] DEVICE FOR ENHANCING FLUORESCENCE AND KINETICS AND METHODS OF USING THE DEVICE

[75] Inventors: Mark L. Sussman, Baltimore, Md.; Stephen G. Wilson, South Bridge, Mass.; Gregory Tice, Lutherville, Md.

[73] Assignee: Becton, Dickinson and Company, Franklin Lakes, N.J.

[21] Appl. No.: 835,009

[22] Filed: Feb. 12, 1992

Related U.S. Application Data

[63] Continuation of Ser. No. 209,677, Jun. 20, 1988, abandoned.

[51] Int. Cl.⁵ .............................................. C12Q 1/04
[52] U.S. Cl. .......................................... 435/34; 435/4; 435/29; 435/968; 436/800
[58] Field of Search ...................... 435/29, 4, 34, 968

[56] References Cited

U.S. PATENT DOCUMENTS

| | | | |
|---|---|---|---|
| 4,780,423 | 10/1988 | Bluestein et al. | 436/800 |
| 4,868,106 | 9/1989 | Ito et al. | 436/800 |
| 4,919,890 | 4/1990 | Arai et al. | 422/57 |
| 4,959,305 | 9/1990 | Woodrum | 422/58 |
| 4,965,087 | 10/1990 | Wolfbeis | 422/57 |

*Primary Examiner*—Sam Rosen
*Attorney, Agent, or Firm*—Royal N. Ronning, Jr.

[57] ABSTRACT

A carrier having at least one kinetics and fluorescence enhancing support and a dry substance selected from the group consisting of fluorogenic substrates, B methylumbelliferone, 7-amino-4-methyl coumarin, B-napthylamine, fluoroscein, and resorufin deposited on the support demonstrates substantial enhancement of hydrolysis kinetics and fluorescence over pure liquid systems. When the device has a plurality of supports and the supports have different fluorogenic substrates an enzyme rate-of-reaction profile representative of a microorganism in the suspension can be determined and used to identify the organism. The device can also be used to characterize enzymes expressed by other biological specimens.

15 Claims, 8 Drawing Sheets

DEVICE FOR ENHANCING FLUORESCENCE AND KINETICS AND METHODS OF USING THE DEVICE

This application is a continuation of application Ser. No. 07/209,677, filed Jun. 20, 1988, now abandoned.

The present invention relates generally to a device for detecting fluorescence. The device may be used to rapidly identify bacteria and other organisms and to determine enzyme profiles of other biological specimens.

BACKGROUND OF THE INVENTION

Enzymatic hydrolysis of fluorogenic substrates to yield a detectable fluorescent species is known to be useful in a variety of diagnostic applications. For example, a number of researchers have investigated the possibility of using a panel of fluorogenic substrates to determine which enzymes are present in a sample containing an unidentified microorganism and correlating the profile to known profiles to identify the unknown microorganism. Notwithstanding the desirability of using this fluorogenic detection system, widespread use of it has not been adopted for a variety of reasons which make it impracticable.

When laboratories identify organisms from clinical isolates an important goal is rapid identification. Most commercial bacterial identification systems require 18 to 24 hours or longer following isolation of an organism to achieve identification. Some of the current "rapid" systems take 3 to 13 hours. These systems generally rely upon the detection of acidic or basic by-products of sugar or amino acid metabolism produced following a period of organism growth.

One method for identifying specific bacterial species using enzymatic cleavage of substrates is described in U.S. Pat. No. 4,603,108 to Bascomb. The Bascomb patent describes a kit containing tests for 26 constitutive enzymes. In each test the enzyme is determined by its ability to interact with a specific substrate. A test card or other apparatus has a plurality of wells or compartments which separately contain specific substrate solutions for each of the enzyme tests together with other reagents for the tests. In use a bacterial suspension is added to each compartment and a detectable product is developed after a relatively short incubation period. The amount of the corresponding enzyme in each sample is then determined by spectrometric analysis using either colorimetry or fluorimetry.

Another procedure described in the patent uses 7 tests for rapid differentiation of commonly encountered bacterial groups. Bascomb teaches that either the 26 test assay or the 7 test assay gives a unique fingerprint for the species or group of species. A quantitative determination of enzyme activity for each group or species can be used to identify the group or species by comparison to activity profiles of previously identified bacteria. The specific tests described determine activity by detecting absorbance in a flow cell. Discrete sample analysis and continuous flow analysis can be used. The method of the Bascomb patent requires a large biomass and a high fluid volume as well as a relatively long incubation time.

Other scientists have used fluorogenic substrates to identify microorganisms. Westley, J. W. et al, discuss the use of alpha-amino acid B napthylamide substrates for identification of 24 strains of bacteria ("Aminopeptidase Profiles of Various Bacteria"; *Appl. Micro.*, 15:822–825, 1967). Bacteria were suspended in solution and incubated with substrate solutions. The fluorescence of the released B-napthylamine was measured after 4 hours of incubation.

Another paper describing the use of fluorometric analysis to measure enzyme hydrolysis of 19 L-amino acid B-napthylamides is Peterson, E. W. et al., "Rapid Detection of Selected Gram-Negative Bacteria by Aminopeptidase Profiles"; *J. Food Sci.*, 43:1853–1856 (1978). A profile for each culture was obtained in 4 to 6 hours.

A review of the literature pertaining to use of fluorogenic substrates to profile microbial enzyme activity is contained in Godsey, J. H. et al., "Rapid Identification of *Enterobacteriaceae* with Microbial Enzyme Activity Profiles"; *J. Clin. Micro.*, 13:483–490 (1981). The Godsey group reports use of eighteen fluorogenic substrates in a study of 539 strains of the family Enterobacteriaceae. Hydrolysis rates were monitored for the first 30 minutes in 2 ml of buffer containing substrate at 37° C. All substrates except urea were derivatives of B-methylumbelliferone, B-napthylamine or 7-amino 4-methyl coumarin.

In U.S. Pat. No. 4,591,554, to Koumara et al, fluorescence analysis using umbelliferone derivatives is described as a method to detect and determine the number of small numbers of microorganisms. In the method an umbelliferone derivative is added to a sample solution and the mixture solution is incubated. Thereafter, insoluble residues (e.g. cells) are removed and fluorescence is read in a conventional detector. The amount of fluorescence is then related to the number of microorganisms. The examples describe experiments where a solution containing the substrate is mixed with a solution containing bacteria. After incubation the pH is adjusted and the mixture is centrifuged to remove insoluble cells. Thereafter the fluorescence of any liberated 4-methylumbelliferone is determined. In some cases coenzymes are used. In other cases the cells are disrupted to increase the amount of liberated enzymes.

Fluorogenic substrates are also known to be useful to assay extracellular enzymes present in living organisms (Snyder, A. et al., "Pattern Recognition Analysis of In-Vivo Enzyme Substrate Fluorescence Velocities in Microorganism Detection and Identification"; *App. & Enviro Micro,* 51:969–977 (1986)). Reaction times were fifteen minutes or less. Assays were carried out in 2 ml buffer. This work also forms the basis of an International Patent Application entitled "Viable Microorganism Detection by Induced Fluorescence" with the University of Cincinnati as applicant (Int'l Pub. No. WO 86/05206 dated Sep. 12, 1986).

Yet another technique to fingerprint bacteria based on the differences in enzyme content and activity is described in Chou Pong Pau et al, "A Rapid Enzymatic Procedure for Fingenprinting, Bacteria by Using Pattern Recognition of Two-Dimensional Fluorescence Data"; *Clin. Chem.* 32:987–991 (1986). In that system a mixture of 6 fluorogenic substrates is used, each with a different fluorescent moiety. Fluorescence increases are monitored over a 30-minute period. A Fourier transformation of the fluorescence data is used to produce a two dimensional array which is characteristic of each test organism. This method requires the use of complicated and expensive equipment to perform the measurements and to execute the mathematical transformation.

Use of free fluors in diagnostics is well known. Many free fluors are known to be quenched or enhanced by variations in enviromental conditions such as pH, redox potential or oxygen partial pressure. These fluors are used to detect or monitor the enviromental condition that affects their fluorescence.

Each of the methods described above to identify or quantify the amount of analyte present in a sample by detecting or monitoring enzyme hydrolysis of a fluorogenic substrate requires an aqueous environment. Similarly, when free fluors are used to monitor enviromental changes in a biological test system, an aqueous environment is required. Problems arise in designing aqueous test systems using free fluors or fluorogenic substrates and having acceptable shelf lives because free fluors and fluorogenic substrates need dry conditions to best maintain their stability. Thus one design challenge is the problem of providing the free fluor or fluorogenic substrate in a dry state.

When fluorogenic substrates are stored dry, they need to be available to react with the enzyme so that they rapidly reach a steady-state reaction following addition of an aqueous test suspension or solution. This challenge is not easily met because fluorogenic substrates show various solubilities in water. The least water soluble are generally the lipase substrates. This challenge is particularly difficult for those substrates having low aqueous solubility.

One material that has been used as a support for fluorescent materials is cellulose filter paper. Whatman No. 4 paper was used for analysis at 4° K. of pyrene, benzo[a]pyrene, chrysene and solvent-refined-coal by Tuan Vo Dinh, "Fluorescence Line Narrowing Spectrometry of Polycyclic Compounds on Filter Paper Substrates"; *Anal. Chem.* 58:3135–3139 (1986).

One susceptibility testing product line uses filter paper to store fluorogenic substrates. In Sensititre TM Susceptibility panels a product of Radiometer of Copenhagen, Inc., Copenhagen, Denmark) fluorogenic substrates are provided dry on filter paper. In use, the filter paper strips are placed in broth and the fluorogenic substrate is eluted into solution. Thereafter the broth is dispensed into microwells where the solution susceptibility test is performed.

Another problem encountered when characterizing an enzyme profile to identify a microorganism or a pathological state is the problem of inadequate biomass. Desirably in microorganism identification tests, the microorganism to be identified is obtained from an isolated colony from an overnight streak plate prepared from a clinical sample, or directly from a positive blood culture vial. In both of these circumstances the number of microorganisms available is limited. Similarly when a biological sample is tested for endogenous enzyme content, the amount of biological fluid or tissue available for analysis may be limited. Thus the amount of biomass needed to perform the characterization should be minimized. To achieve rapid results, a high biomass concentration is necessary. To satisfy these two criteria, a test system should be miniturized to the extent reasonably possible. Miniaturization to allow use of a small biomass causes another problem. With a given amount of fluorogenic substrate and available enzyme concentration, miniturization of the system reduces the amount of substrate hydrolized per unit time. The total fluorescence change per unit time is also reduced.

Thus a need exists for a miniaturized system which has an acceptable shelf life, requires a small biomass of sample, provides fast equilibration to steady-state kinetics following addition of sample, and yields an enhanced fluorescence signal.

SUMMARY OF THE INVENTION

The device of the present invention has a carrier having at least one kinetics and fluorescence enhancing support mounted on or in it. The kinetics and fluorescence enhancing support has deposited on it a dry substance selected from the group consisting of fluorogenic substrates, B-methylumbelliferone, 7-amino 4-methyl coumarin, B-napthylamine, fluoroscein, and resorufin. The kinetics and fluorescence enhancing support has a surface area sufficiently large to retain an effective amount of the dry substance.

Preferably the device has a plurality of kinetics and fluorescence enhancing supports and the dry substance is a fluorogenic substrate. In a particularly preferred embodiment, the kinetics and fluorescence enhancing supports are made of a material having a high surface area-to-volume ratio. Most preferably, the surface area and void volume should be sufficient to carry an effective amount of the dry substance which is available for wetting with an aqueous sample received in the void volume of the support.

The dry substance is conveniently deposited on its kinetics and fluorescence enhancing support by dissolving it in a suitable anhydrous solvent and depositing the solution on the kinetics and fluorescence enhancing support. The solvent is removed by suitable means, such as vacuum dessication. Alternatively, a solution of the substance can be absorbed into its kinetics and fluorescence enhancing support and the kinetics and fluorescence enhancing support has a surface area-to-volume ratio sufficient to leave a void volume to receive the specimen to be analyzed. The kinetics and fluorescence enhancing support having its dry substance dried on it may then be stored, preferably in a low humidity and low temperature environment, for extended periods of time.

The enzyme characterization method of the present invention utilizes a dry substance selected from the group of fluorogenic substrates, B-methyumbelliferone, 7-amino 4-methyl coumarin, B napthylamine, fluoroscein, and resorufin to determine rapidly the level of one or more enzymes or to determine a profile of enzymes extant in a biological specimen. The method is useful to screen for disease states (e.g., excessive alkaline phosphatase in seminal fluid is indicative of prostate cancer) and to identify an organism present in the specimen. In most cases, the organisms being determined will be bacteria. However, other microorganisms, such as fungi, can also be identified. The method of the invention may also be useful to characterize the enzyme profiles of a variety of biological specimens including suspensions of microorganisms and body fluids or dispersed tissue samples. It may also be used to detect antibiotic susceptibility and minimum inhibitory drug concentration for a selected organism by using fluorogenic substrates, free fluors, or both in combination with varying concentrations of selected antibiotics to detect the presence or absence of organism metabolism or growth.

In the enzyme characterization method of the present invention, a fluid sample is added to one or more of a plurality of kinetics and fluorescence enhancing supports. Each kinetics and fluorescence enhancing support has dried on it a fluorogenic substrate or a fluor selected form the group consisting of B-umbelliferone, 7-amino-4-methyl coumarin, B-napthylamine, fluoroscein, and resorufin. The enzymes present in the sample hydrolize their substrates. If the substrates are fluorogenic, the hydrolysis rates are determined by measuring the rate of fluorescent product production. If the substrate is not fluorogenic, the kinetics and fluorescence enhancing support has deposited on it an enzyme substrate and a dry free fluor that is enhanced or quenched in the presence of a hydrolysis product (e.g. acid, base, $O_2$). In this manner the presence of the enzyme that hydrolizes the particular substrate is detected and if desired a rate of- reaction profile of one or more enzymes in the sample is established. The enzyme rate-of-reaction profile of the sample is then analyzed.

In the case of microorganism identification, the rate-of-reaction profile is compared with reference enzyme rate-of-reaction profiles of known microorganisms in order to identify the unknown microorganism. In antibiotic susceptibility and minimum inhibitory concentration testing, an absence of enzyme activity in the presence of antibiotics as compared to the presence of enzyme activity of a control sample is indicative of antibiotic effectiveness.

When the kinetics and fluorescence enhancing supports of the present invention are used with dried fluorogenic substrates which are contacted with their enzymes in a fluid sample, substantial enhancement of the enzyme-substrate interaction is observed. The kinetics of the enzyme substrate interaction are enhanced in that rapid equilibration to steady-state kinetics is observed. Substrates which are readily water-soluble rapidly dissolve. These substrates thereby rapidly reach steady-state kinetics. Surprisingly, even those fluorogenic substrates considered to have marginal water solubility rapidly reach steady-state reaction conditions. Substrates having low solubility display a high enzyme-specific reaction rate upon contact with a fluid biological specimen if they have been deposited upon a kinetics and fluorescence enhancing support of appropriate character.

Another advantage of the kinetics and fluorescence enhancing supports of the invention is that they greatly enhance fluorescence when compared to the fluorescence of the same fluor when measured in a purely liquid environment. Surprisingly, an interaction between the fluor and the support causes considerable amplification of fluorescence. This observation is contrary to anticipated results because scattering and absorption should reduce the intensity of the exciting radiation that reaches the fluor at any depth within the solid support. Similarly, the intensity of the emitted fluorescent light produced at any depth in the solid support should also be reduced because of scattering and absorption by the support. Thus an external fluorescent signal obtained from a clear solution of fluor that has been absorbed into a solid support and excited by a given intensity of exciting radiation should be less intense than a signal obtained from an illumination of the clear solution alone with an identical excitation energy. In the present invention with a suitable choice of material for the kinetics and fluorescence enhancing support, the fluorescent signal becomes many times larger when a fluor solution is absorbed into the solid support.

DETAILED DESCRIPTION OF THE INVENTION

Figure 1:
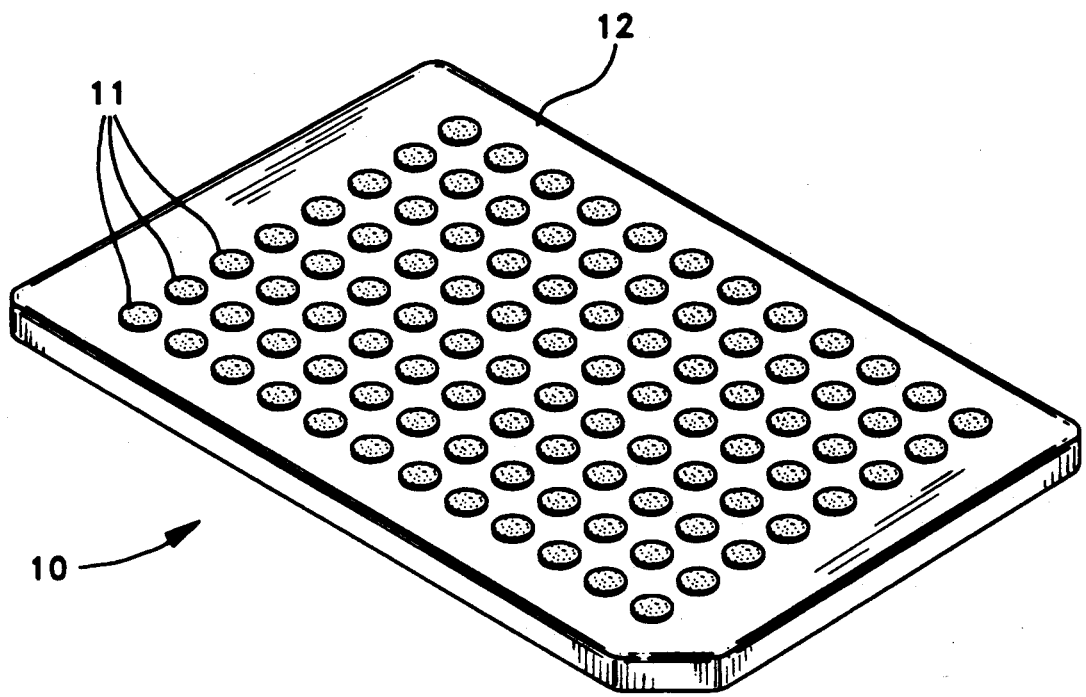
FIG. 1 shows a preferred construction of the device of the present invention with the kinetics and fluorescence enhancing supports secured to a planar support.
Figure 2:
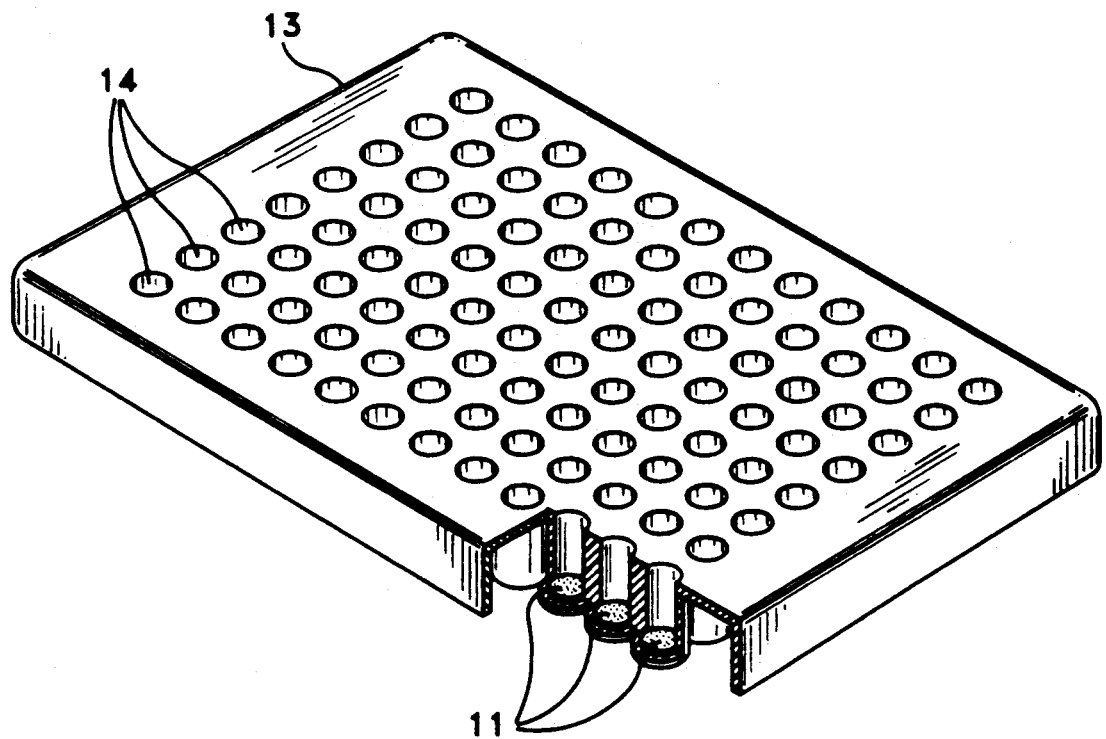
FIG. 2 shows an alternative construction of the device of the present invention with the kinetics and fluorescence enhancing supports in test wells.

As shown in FIG. 1 the preferred test device 10 of the present invention is prepared by securing an appropriate number and array of kinetics and fluorescence enhancing supports 11 onto a carrier 12 such as a card or other surface support. The carrier is preferably (but not necessarily) rigid and planar. Suitable materials include polyethylene, polypropylene, polyvinyl chloride, acrylonitrile butadiene-styrene, fluoropolymers, polycarbonates, and acrylics. Polypropylene is preferred.

Alternatively, the carrier may be a tray 13 or strip having a plurality of test wells 14, i.e. a conventional microwell tray or strip. In this case the device is assembled by placing the kinetics and fluorescence enhancing supports 15 in the individual test wells 14 in a suitable array and number for the intended application.

Selection of a suitable material for the kinetics and fluorescence enhancing support involves several considerations. In general, the kinetics and fluorescence enhancing support should not be reactive with the dry fluorogenic substrate or free fluor deposited on it; the kinetics and fluorescence enhancing support should preferably have properties which enhance fluorescence and should itself not exhibit substantial fluorescence; the kinetics and fluorescence enhancing support should have a surface area-to-volume ratio sufficient to retain an effective amount of dry substrate or free fluor and preferably to receive a sample suspension or solution; the kinetics and fluorescence enhancing support should be sufficiently hydrophilic to be wettable by a fluid sample; and the kinetics and fluorescence enhancing support should have a large number of sites capable of retaining hydrophobic materials. Suitable materials for use as the kinetics and fluorescence enhancing support of the present invention include alpha cellulose and pH neutralized glass fiber. Particularly preferred are alpha cellulose in the form of cotton lint paper (e.g. paper nos. 740-E and 903 available from Schleicher & Schuell, Keene, NH) and a support matrix available in R&D quantities under the designation Hydrophilic HDC ™ (Pall BioSupport Corp., Glen Cove, NY).

In general, the thickness and surface area of the kinetics and fluorescence enhancing support are influential criteria in the optimization of the methods of the invention. Where the kinetics and fluorescence enhancing support has a substrate deposited on it, the thickness of the kinetics and fluorescence enhancing support should be sufficient to carry an effective amount of substrate for reaction with the available enzyme or enzymes present in a sample. Similarly where the support is supplied with only dry free fluor deposited on it, preferably the thickness is sufficient to receive the remaining components of the intended reaction system during the process. In general, a thickness of from 0.1 mm to 2.0 mm is suitable. A thickness of 0.2 mm to 1.0 mm can be used conveniently, and a thickness of from 0.5 mm to about 0.9 mm is preferred. The thickness, in cooperation with the surface area, determines the volume of fluid required to completely wet the kinetics and fluorescence enhancing support.

The shape of the kinetics and fluorescence enhancing support is not critical. Conveniently the kinetics and fluorescence enhancing support is formed as a right circular cylinder (disk) having a diameter of from about 1.0 mm to about 10.0 mm which corresponds to a superficial area available for retaining dry substrate, free fluor, or both of about 0.8 mm$^2$ to about 80 mm$^2$. A void volume of the kinetics and fluorescence enhancing support from 1 ul to 100 ul is suitable. Void volumes between 1 ul to 75 ul can be used. The void volume is preferably from about 1 microliter (0.001 cc) to about 25 microliters (0.025 cc).

The substrates useful in the present invention are those fluorogenic and non-fluorogenic substrates which have been found to be reactive with enzymes present in the sample. The fluorogenic substrates are usually selected from fluorogenic analogs of organic and inorganic acids, glycosides and peptides.

When the enzyme characterization method of the invention is used to identify microorganisms, use of the same fluor to prepare each of the fluorogenic substrates is preferred, although different fluors may be used for different substrates. The fluor is coupled to the natural substrate moiety by any suitable means, usually by covalent binding. Suitable fluors may include, but are not necessarily limited to B-methylumbelliferone, 7-amino-4-methyl coumarin and other like coumarin derivatives, beta napthylamine derivatives, and like adducts of resorufin and fluorescein.

The kinetics and fluorescence enhancing supports of the invention are preferably prepared by dissolving the fluorogenic substrate or free fluor in a suitable solvent, such as dimethylsulfoxide or chloroform. The dissolved substrate or free fluor is deposited upon its kinetics and fluorescence enhancing support. After the solution is deposited upon the kinetics and fluorescence enhancing support, the solvent may be removed by suitable means such as vacuum dessication. In this manner the substrate is retained on the kinetics and fluorescence enhancing support. The kinetics and fluorescence enhancing supports may then be stored, preferably under conditions of low temperature and low humidity for extended periods of time.

The preferred device has the kinetics and fluorescence enhancing supports mounted onto a card. This embodiment eliminates the need to place the fluid in a well or container. In one preferred form of the invention, cellulose sheets are coated with an adhesive on one side and are stamped through a die onto a planar plastic polypropylene support, leaving separated cellulose disks affixed to the plastic surface. After the disks have been coated with fluorogenic substrate or free fluor and dried, a fluid solution or suspension may then be placed directly on each disk, and the fluorescence read instrumentally. When the fluid volume employed is less than or approximately equal to the volume of fluid necessary to saturate the disk, no well or container is necessary to contain the fluid.

The enzyme characterization method of the present invention allows for the rapid identification of microorganisms isolated from clinical samples. Such clinical samples may include urine, stool, wound, throat, genital samples, or normally sterile body fluids such as blood or cerebral spinal fluid. The microorganisms are usually isolated from the specimen prior to identification.

Colonies of bacterial cultures, when prepared from the biological specimen, are harvested after a sufficient period of growth (usually about 18 hours). The harvested colony is suspended in a suitable aqueous liquid for identification by the method of the invention. The prepared suspension of microorganisms or the biological specimen is deposited directly on the kinetics and fluorescence enhancing supports.

While the assay may be performed with intact cells, some treatment of the cells to increase enzyme availability may be desirable. For example, low levels of a detergent may be used to increase cell membrane permeability. As an extreme example, complete disruption of the cell membrane may be desirable. Any suitable known treatment may be used to affect the cell membrane in the desired manner.

The number of kinetics and fluorescence enhancing supports required to identify a particular microorganism will depend on the microorganism. In some cases, a single support may be enough. In other cases, forty or more different supports may be required to differentiate one microorganism from another having a very similar profile.

In the enzyme characterization method a fluid sample, regardless of the method of preparation, is deposited onto each of the kinetics and fluorescence enhancing supports. As indicated, each kinetics and fluorescence enhancing support differs from others either in the identity of the fluorogenic substrate (or free fluor) or its concentration. Preferably the kinetics and fluorescence enhancing support is saturated with the sample while free fluid on the surface of the kinetics and fluorescence enhancing support is minimized. Typical saturation volumes for kinetics and fluorescence enhancing supports within the preferred size range are from about 3 microliters to about 25 microliters.

After a suitable period of time, generally from about 2 minutes to about 30 minutes, the degree of reaction of an enzyme with each of the substrates is determined by examination of each kinetics and fluorescence enhancing support with a fluorometer using appropriate excitation and emission wavelengths for the particular fluor.

A profile of reaction rates of enzymes with the plurality of fluorogenic substrates is then determined and the resulting profile is compared with reference rate profiles of known microorganisms to identify the particular microorganism for which the profile was generated.

An initial fluorescence reading is taken as soon after inoculation as convenient for each kinetics and fluorescence enhancing support using epifluorescence techniques, with excitation and emission wavelengths selected appropriately for the particular fluor. Subsequent readings are then taken at selected intervals of time. One minute intervals, or some other appropriate time period, are used to accumulate fluorescence readings over a period of incubation which can conveniently range from 2 minutes to 30 minutes.

Rates-of-reaction can then be determined for each of the kinetics and fluorescence enhancing supports. These rates may be normalized to the turbidity of the sample suspension. Due to the wide range of the resultant fluorescence intensities observed from such reactions, use of a variable photometer detection sensitivity for some of the substrates utilized is preferred. One means of providing this variable sensitivity is to change the high voltage applied to the photomultiplier tube used to monitor the fluorescent emission. This adjustment may be either manually or automatically controlled. Normalizing the reaction rates relative to the sensitivity employed to monitor the reaction is also preferred.

When using the method to identify an unknown microorganism, a rate profile for all of the kinetics and fluorescence enhancing supports is generated and then compared to the previously established rate profiles from a database of known organisms. An appropriate algorithm may then be employed to determine the best-fit identification of the unknown microorganism. For example, in one identification method, the probability that a particular reference strain will yield a substrate hydrolysis rate within a given range of rates is determined for each substrate of the plurality of substrates. Then the actual hydrolysis rates of an unknown organism are compared to a database containing the probabilities for each of the reference strains to determine a likelihood that the unknown is a member of each of the particular reference strains. The likelihoods thus determined are then normalized for the unknown by dividing the likelihood that the unknown is the same species as the reference species by the sum of the likelihoods for all the reference species. These normalized likelihoods are then multiplied by 100 to express them as percentages. The reference strain having the highest percentage likelihood is the strain that the unknown is most likely to be. Desirably, all data acquisition and analysis is performed with a computer.

An additional advantage of using the kinetics and fluoroescence enhancing supports of the present invention is more reproducible instrumented measurement of fluid fluorescence. When determining the fluorescence of small volumes of fluid in microwells, the hydrophobicity of the well surface will cause variation in the shape of the meniscus affecting accuracy of the measurement. Placement of the fluid drop in the well also becomes critical, because very small volumes of fluid do not uniformly cover the bottom of the well. These problems can be partially overcome by the addition of detergents to the diluting fluid or by surface pretreatment of the plastic wells, but these treatments create additional complications for the system (e.g. surfactants affect organism cell membranes).

The use of very turbid bacterial suspensions in conventional systems also affects measurement of fluorescence. In a purely liquid system, these turbid suspensions (approximately MacFarland No. 4 concentration) interfere with the reading of fluorescence by directly scattering and absorbing much of the excitation energy. When the kinetics and fluorescence enhancing supports of the present invention are used, the bacteria become contained within the kinetics and fluorescence enhancing supports. In the system of the present invention highly turbid suspensions exhibit little effect on the desired fluorescence measurement.

The following examples further illustrate various features of the invention, but are intended in no way to limit the scope of the invention which is defined in the appended claims.

EXAMPLE 1

A fluorometer designed to read methylumbelliferone disposed in microwell trays (MicroFLUOR ™ Reader, Dynatech Laboratories, Inc., Chantilly, VA 22021) was used to study the fluorescence characteristics of the free fluors B methylumbelliferone (Sigma Chemical Company, St. Louis, MO 63178) and 7-amino 4-methyl coumarin (Polysciences, Inc., Warrington, PA 18976).

The relationship of concentration and volume to fluorescence was studied with B methylumbelliferone. The fluor was dispensed into black polystyrene microwell trays (MicroFLUOR TM "B" Plates, Catalog No. 011-010-780, Dynatech Laboratories, Inc., Chantilly, VA). The following protocol was observed: 25 ul of fluor, dissolved in reagent alcohol, was dispensed into each test well; the alcohol was allowed to evaporate in a 35° C. incubator until dry; the fluor was reconstituted with 0.1 M HEPPS buffer adjusted to pH 8.0 (United States Biochemical Corporation); the plate was read, and results are given below in Table 1 in terms of relative fluorescence units.

TABLE 1

B-METHYLUMBELLIFERONE RELATIVE FLUORESCENCE AS A FUNCTION OF TOTAL FLUOR PRESENT AND VOLUME OF RECONSTITUTING BUFFER

| Micrograms B-Methyl umbelliferone | Volume of Reconstituting Buffer, (ul) | | | | |
|---|---|---|---|---|---|
| | 50 | 100 | 150 | 200 | 250 |
| 0.0 | 6 | 10 | 15 | 28 | 29 |
| 0.0156 | 54 | 69 | 75 | 84 | 98 |
| 0.0313 | 111 | 135 | 118 | 174 | 174 |
| 0.0625 | 229 | 274 | 254 | 317 | 327 |
| 0.125 | 440 | 536 | 541 | 620 | 640 |

This data shows that the fluorescence signal is directly proportional to the amount of fluor present in the well. Given any single concentration of fluor, a trend of increasing signal with increasing volume is also observed.

As experiment very similar to that described above and using the same protocol was performed, except that the B-methylumbelliferone was deposited on a disk punched from cellulose filter paper (Catalog No. 740-E, Schleicher & Schuell, Inc., Keene, NH 03431) which was placed on the bottom of the well of a black microwell tray (Dynatech's MicroFLUOR TM "B" Plates). Data from this experiment is shown in Table 2.

TABLE 2

B-METHYLUMBELLIFERONE RELATIVE FLUORESCENCE AS A FUNCTION OF TOTAL FLUOR PRESENT AND VOLUME OF RECONSTITUTING BUFFER WITH PAPER DISKS DISPOSED IN EACH WELL

| Micrograms B-Methyl-umbelliferone | Volume of Reconstituting Buffer, (ul) | | | |
|---|---|---|---|---|
| | 25 | 50 | 75 | 100 |
| 0.0 | 207 | 130 | 78 | 90 |
| 0.0156 | 245 | 146 | 169 | 131 |
| 0.0313 | 529 | 304 | 243 | 193 |
| 0.0625 | 1045 | 579 | 478 | 413 |

TABLE 2-continued

B-METHYLUMBELLIFERONE RELATIVE FLUORESCENCE AS A FUNCTION OF TOTAL FLUOR PRESENT AND VOLUME OF RECONSTITUTING BUFFER WITH PAPER DISKS DISPOSED IN EACH WELL

| Micrograms B-Methyl-umbelliferone | Volume of Reconstituting Buffer, (ul) | | | |
|---|---|---|---|---|
| | 25 | 50 | 75 | 100 |
| 0.125 | 2109 | 1231 | 965 | 857 |

NOTE: The values included above for wells containing disks and fluor have had subtracted the fluorescence values measured using wells having blank cellulose disks and a corresponding amount of buffer prior to reading.

As in the case with B-methylumbelliferone in wells with no disks, fluorescence in wells containing cellulose disks is directly proportional to the amount of fluor added for any given volume of reconstituting buffer. However, fluorescence in the presence of cellulose disks decreases with increasing volumes of reconstituting buffer. In fact, the fluorescence observed is nearly proportional to the final concentration (ug/ml) of fluor. This effect is opposite to that seen when no disks are present in the wells of an identical tray. These same trends in fluorescence behavior in the presence of disks were noted in other experiments even when the reconstituting buffer was added in volumes as small as 4, 8, 16, and 24 ul per disk. Approximately 25 ul of fluid is required to saturate a cellulose disk of 0.25 inches diameter.

A similar experiment was repeated using the fluor 7 amino-4-methyl coumarin. The protocol employed was identical to that used in the previously described experiments. Data are presented in Table 3.

TABLE 3

RELATIVE FLUORESCENCE OF 7-AMINO-4-METHYL COUMARIN IN MICROWELLS WITH AND WITHOUT CELLULOSE DISKS AS A FUNCTION OF TOTAL FLUOR AND VOLUME OF RECONSTITUTING BUFFER

| Matrix | Total Coumarin (ug) | Reconstituting Buffer (ul) | | |
|---|---|---|---|---|
| | | 25 | 50 | 100 |
| DISKS | 0.0 | 145 | 99 | 85 |
| | 0.125 | 362 | 226 | 170 |
| | 0.250 | 548 | 299 | 241 |
| | 0.500 | 881 | 528 | 357 |
| NO DISKS | 0.0 | 1 | 2 | 3 |
| | 0.125 | 5 | 8 | 10 |
| | 0.250 | 8 | 13 | 18 |
| | 0.500 | 17 | 23 | 29 |

As had been previously shown for B methyl-umbelliferone in the presence of disks, 7-amino-4-methyl coumarin also yields relative fluorescence values directly proportional to the total amount of fluor present for any given volume of reconstituting buffer. In the presence of cellulose disks the relative fluorescence also decreases with the addition of reconstituting buffer for a given total amount of fluor.

The marked fluorescence enhancement resulting from free fluor addition to cellulose supports is clearly evident when the data with and without disks is compared.

EXAMPLE 2

This example demonstrates that wells or containers are not necessary for reactions to occur between substrate and inoculum when the substrate is dried onto a substrate kinetics and fluorescence enhancing support.

Figure 3:
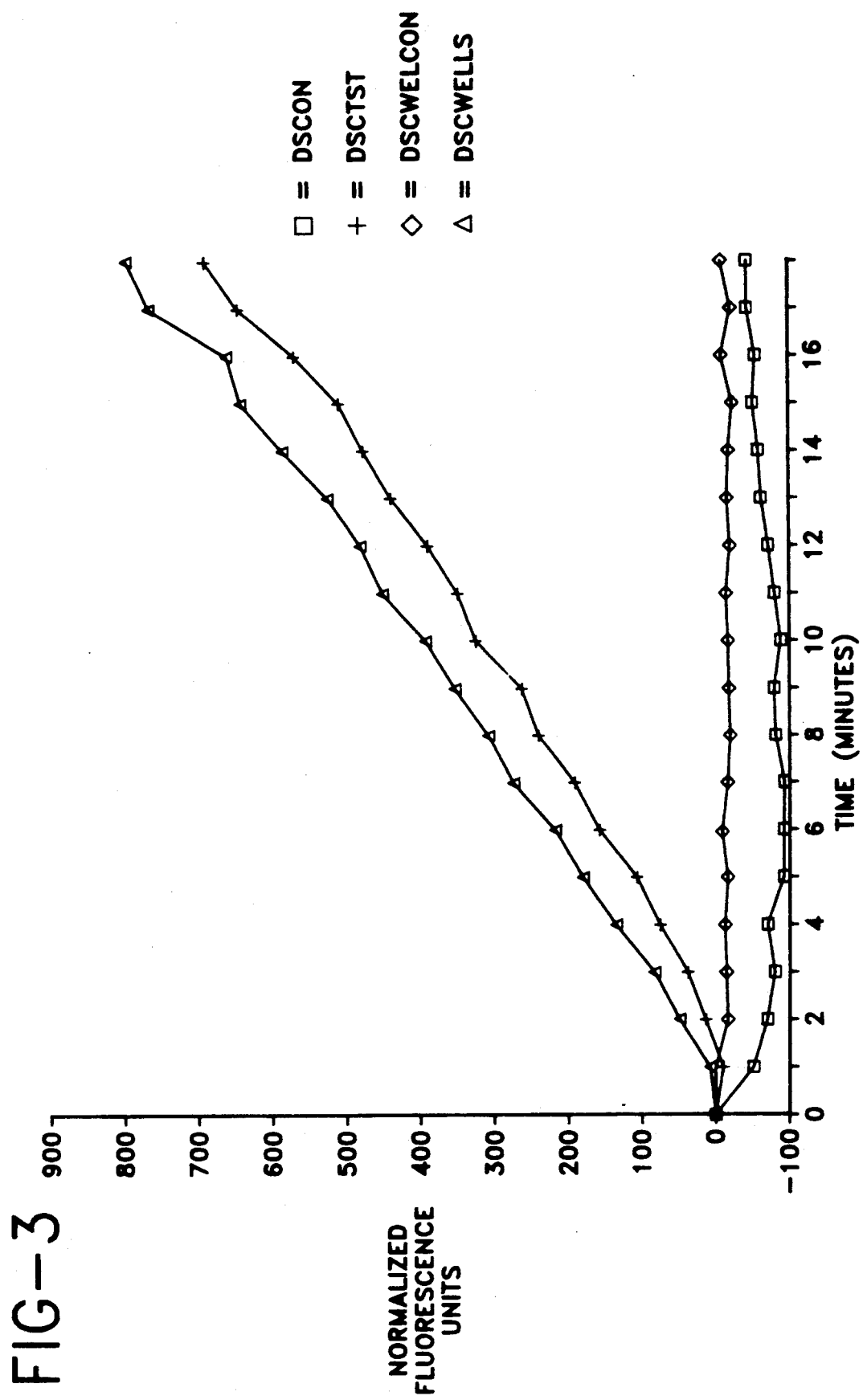
FIG. 3 shows rates of hydrolysis by E. coli of 4-methylumbelliferyl B-D galactoside deposited on kinetics and fluorescence enhancing supports in accordance with the present invention (Example 2)

Aliquots of 20 microliters of a 0.5% solution of 4-methylumbelliferone coupled to B-D-galactoside dissolved in dimethylsulfoxide (DMSO) were added to each of eight cellulose (Catalog No. 740-E, Schleicher & Schuell, Inc. Keene, NH) disks. The DMSO was removed by vacuum dessication. Four of the dried disks were attached to the top of a 96-well, black polystyrene microwell tray using double-sided adhesive tape. The remaining four disks were each placed into the bottom of four wells of the tray. Two of the disks on the tape and two of the disks in the wells of the tray were each inoculated with 25 microliters of a suspension of *Escherichia coli* (ATCC 25922) in 0.1 M TRIS-saline buffer, of pH 7.8. The optical density of the inoculum suspension in a glass tube 16 mm in diameter was 1.8 at 600 nm wavelength as measured with a Spectronic 88 spectrophotometer (Bausch and Lomb, Rochester, NY 14692). The remaining four disks were inoculated with buffer alone to serve as controls. The rate of fluorescence increase for all disks was monitored at one minute intervals using a Dynatech MicroFLUOR ™ reader. As shown in FIG. 3, the observed rates obtained with disks taped on the tray were comparable to those obtained with disks in the wells. Thus, no wells or containers are required to yield satisfactory determination of the rate of fluorescence increase due to substrate/inoculum reaction. By eliminating the need for wells or containers, the size of the physical system can be greatly reduced, as can the inoculum volume required to perform the test.

EXAMPLE 3

Various support materials were tested for the ability to enhance fluorescence and kinetics. To test each support, disks of 0.250 inch (6.4 mm) diameter were punched from sheet stock of each of the materials listed in Table 4. A 20 microliter aliquot of a 0.5% solution of fluorogenic substrate was added to each disk. The substrates tested were 4-methylumbelliferyl phosphate (a buffer soluble substrate) and 4-methylumbelliferyl palmitate (a buffer insoluble substrate). The disks containing substrate were dried by vacuum dessication and were then placed into wells of a 96 well, black polystyrene microwell tray (Dynatech MicroFLUOR ™ "B"). Each disk was inoculated with a suspension of *Pseudomonas aeruginosa* (ATCC 27853) in 0.1 M TRIS-saline buffer, pH 7.8. The cell density of the organism suspension as measured in a 16 mm diameter tube was adjusted to an optical density of 1.8 at 600 nm. Control disks were inoculated with buffer alone. The rates of fluorescence increase were monitored at one-minute intervals with a MicroFLUOR ™ reader.

The results obtained with all the supports are summarized in Table 4. The synthetic supports produced poor reactions with the hydrophobic palmitate substrate. The nylon supports tended to destabilize the palmitate. Glass fiber supports either inhibited reactions or caused breakdown of the substrate. The cellulose substrates produced the best differentiation of organism rates from control rates of reaction. The 4-methylumbelliferyl palmitate hydrolysis rates obtained with organisms also tended to be higher and more consistent with the cellulose supports than with the other supports, and the cellulose support did not destabilize this substrate.

TABLE 4

SUPPORT TEST RESULTS

| Support | Description | Test Result |
|---|---|---|
| Durapore[a] | Polyvinylidene difluoride | No palmitate rates |
| Pdt. 8-S[b] | Nonwoven | No palmitate rates |

TABLE 4-continued

| SUPPORT TEST RESULTS | | |
|---|---|---|
| Support | Description | Test Result |
| Pdt. 5-S[b] | Synthetic Nonwoven | No palmitate rates |
| Cellulose[c] | Synthetic Depth Filter | Dissolved in DMSO |
| Ultrapore[d] | Membrane | No palmitate rates |
| Carboxydyne[d] | Membrane | High palmitate controls |
| Nylon 66[b] | Membrane | High palmitate controls |
| Magna Nylon[e] | Nylon 66-polyester | High palmitate controls |
| GD120[f] | No organics | Inconsistent Results |
| Glass Filter[d] | No organics | No phosphate, palmitate rates |
| Microfiber[f] Glass A/E | No organics | High controls |
| Extra Thick[g] | Binders | High controls |
| No. 27[f] | Prefilter | Consistent rates |
| 740E[b] | Cotton Linters | Consistent rates |
| RC60[b] | Regenerated Cellulose | Consistent rates |
| TL Chromatography[b] | Cellulose on Estar Base | Consistent rates |

[a] Millipore (Bedford, MA)
[b] Schleicher & Schuell (Keene, N.H.)
[c] American Filtrona (Richmond, VA)
[d] Pall BioSupport (Glen Cove, NY)
[e] Fisher Scientific (Pittsburgh, PA)
[f] MicroFiltration Systems (Dublin, GA)
[g] Gelman Sciences (Ann Arbor, MI)
[h] Eastman Kodak (Rochester, NY)

EXAMPLE 4

This example shows that the observed rates of fluorogenic substrate hydrolysis are greater with substrates dried onto the kinetics and fluorescence enhancing supports of the present invention than with substrates dried onto the bottoms of microwells.

Aliquots of 20 microliters of a 0.5% solution of 4-methylumbelliferyl palmitate in pure DMSO were added to each of twelve cellulose disks (Cat. No. 740 E, Schleicher & Schuell) and to each of twelve empty wells of a black polystyrene, 96-well microwell tray (Dynatech MicroFLUOR ™ "B"). The DMSO was removed from the disks and tray by vacuum dessication. The disks containing substrate were placed into each of 12 empty wells of the tray. Eight of the wells having substrate-containing disks and eight of the wells containing dessicated substrate alone were each inoculated with 100 microliters of a suspension of Pseudomonas aeruginosa (ATCC 35032) in 0.1 M TRIS-saline buffer, pH 7.8. The cell density of the inoculum was adjusted to a value of 1.76 at 600 nm as measured in a 16 mm diameter tube. The remaining wells with disks and wells containing substrate received buffer without organism so as to serve as controls.

Figure 4:
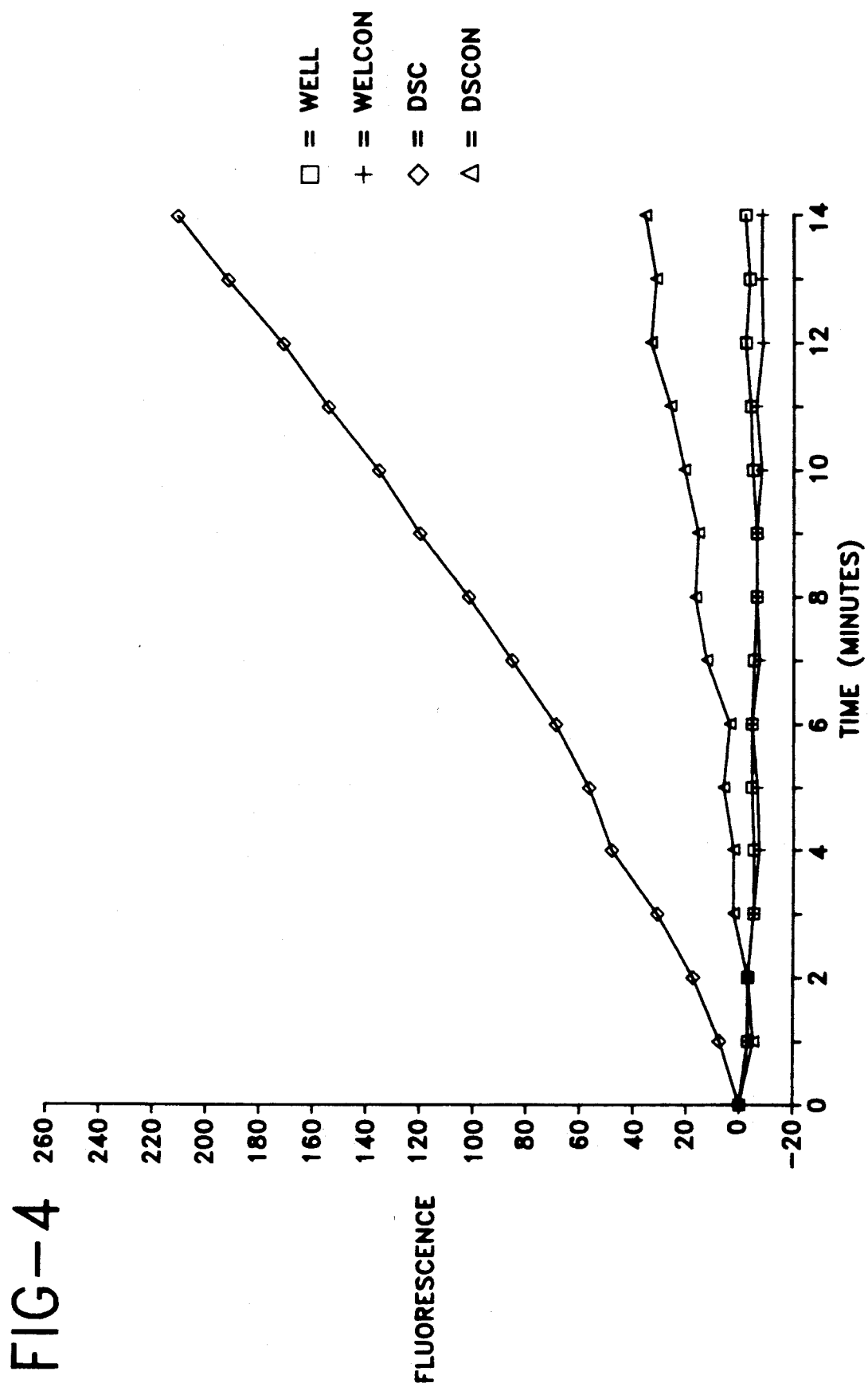
FIG. 4 shows rates of hydrolysis by P. aeruginosa of 4-methylumbelliferyl palmitate deposited in microwells and deposited on kinetics and fluorescence enhancing supports in accordance with the present invention (Example 4)

The rates of substrate hydrolysis were determined by monitoring the fluorescence increase at one-minute intervals with a MicroFLUOR ™ reader (Dynatech). As shown in FIG. 4, the rates obtained with the substrate dried on cellulose disks were considerably higher than those obtained with the substrate dried into the wells directly. Without intending to be bound by any theory, one reason for this enhanced fluorescence may be the larger surface area presented by the disk for substrate deposition and subsequent substrate/inoculum interaction, since the 4-methylumbelliferyl palmitate is buffer insoluble, and thus would be expected to undergo enzymatic hydrolysis primarily at the interface between the substrate at the surface of the support and the liquid inoculum.

Figure 5:
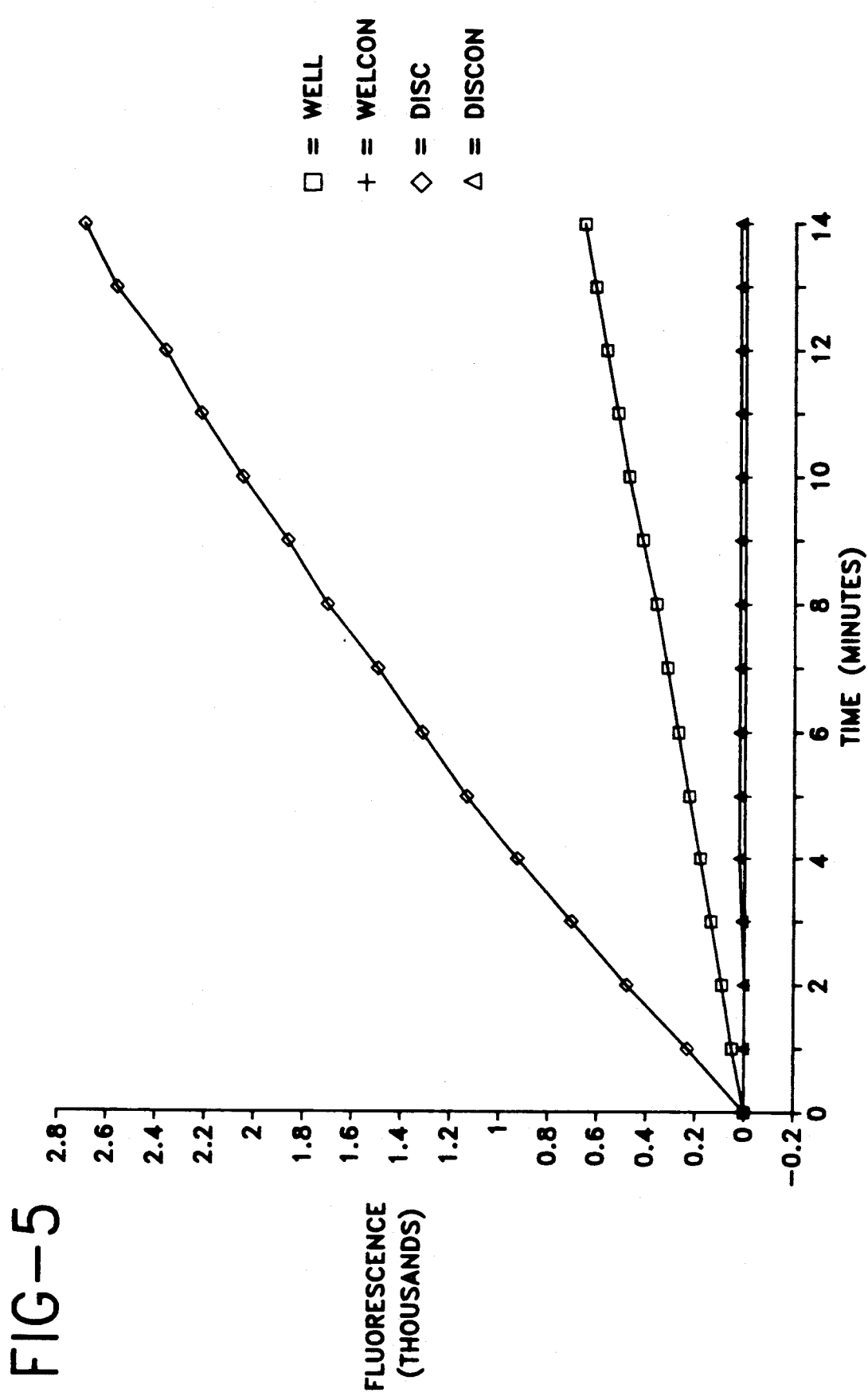
FIG. 5 shows rates of hydrolysis by K. pneumoniae of 4-methylumbelliferyl phosphate deposited in microwells and deposited on kinetics and fluorescence enhancing supports in accordance with the present invention (Example 4)

In a similar experiment to that listed above and employing the same protocol, evidence for fluorescence enhancement by the cellulose disks in reactions involving the buffer soluble substrate, 4-methylumbelliferyl phosphate, is also provided. The disks and wells containing substrate were inoculated with the organism Klebsiella pneumoniae (ATCC 33495). As shown in FIG. 5, the rates observed with substrate dried onto cellulose disks were observed to be much higher than with substrate dried directly into the tray wells.

This example provides direct evidence that the kinetics and fluorescence enhancing supports substantially improve reaction rates with both buffer soluble and buffer insoluble fluorogenic substrates. Thus the use of cellulose disks provides the ability to rapidly attain and then maintain steady-state reactions with this invention.

EXAMPLE 5

Figure 6:
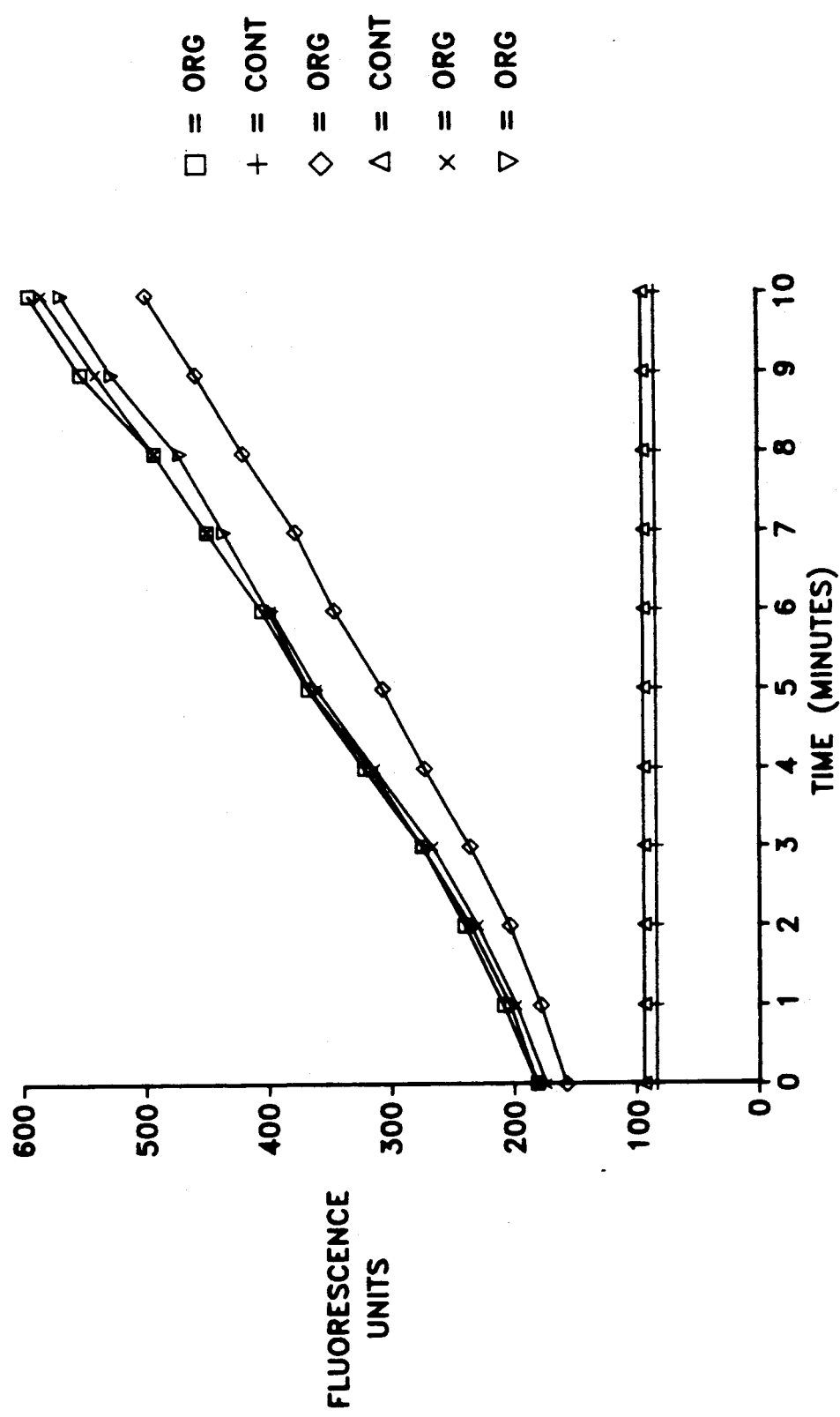
FIG. 6 shows the rate at which S. Marcescens hydrolizes L-leucine-7-amido-4-methyl coumarin (Example 5)
Figure 7:
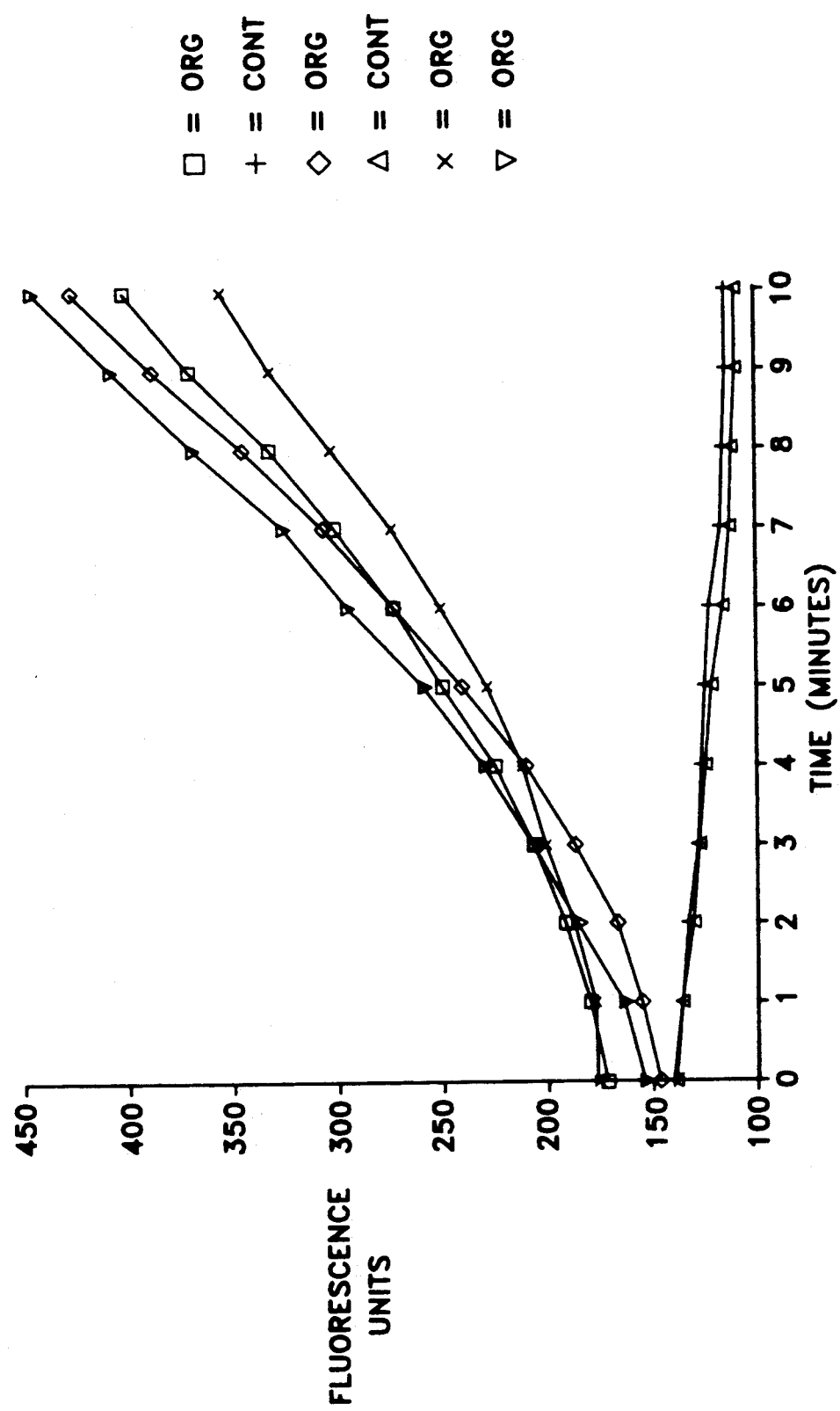
FIG. 7 shows the rate at which S. Marcescens hydrolizes L-phenylalanine-7-amido-4-methyl coumarin (Example 5)
Figure 8:
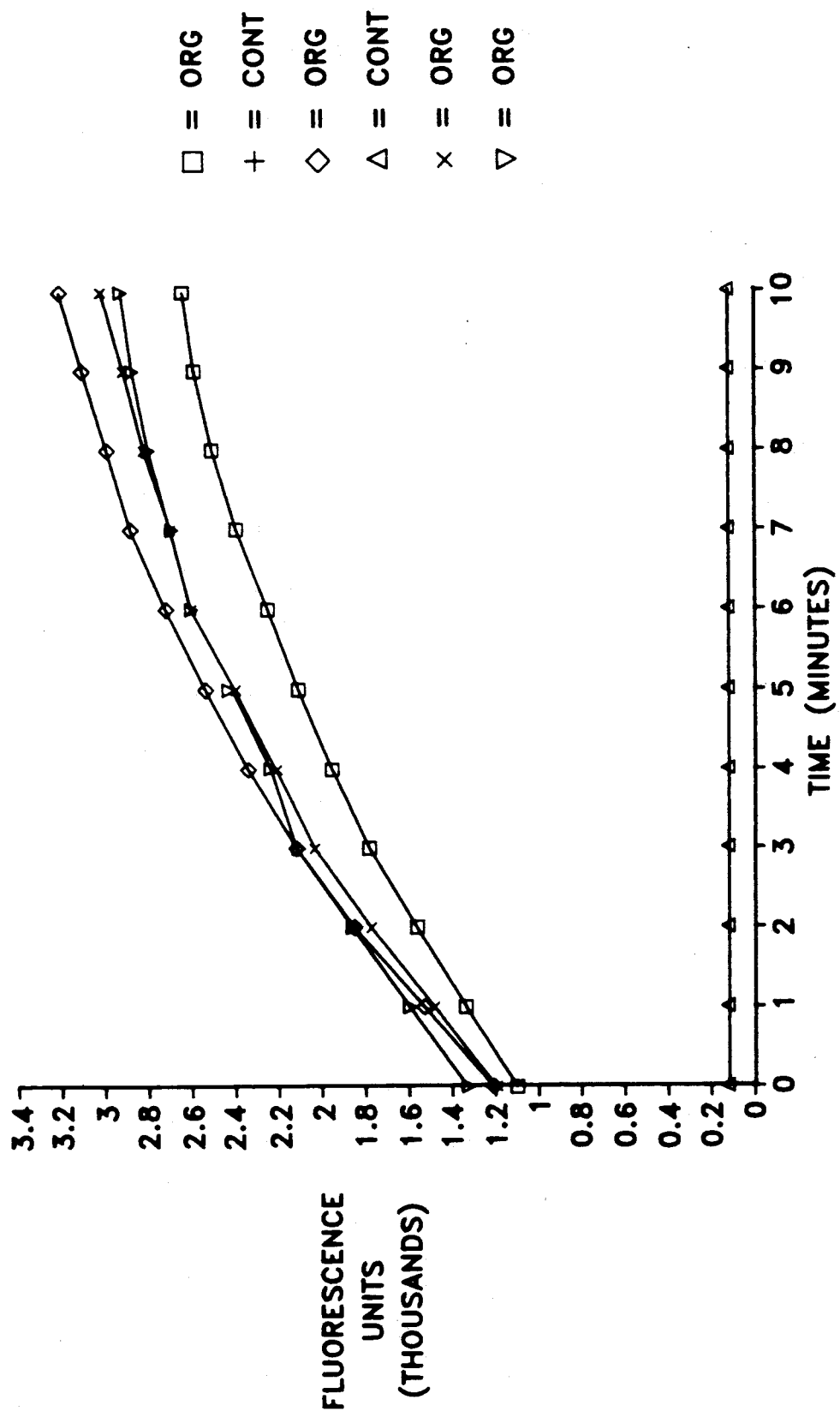
FIG. 8 shows the rate at which S. Marcescens hydrolizes L-alanine-7-amido-4-methyl coumarin (Example 5)

The following example illustrates a variety of rate kinetics which have been observed using the enzyme characterization method of the present invention. Paper disks (No. 740 E, Schleicher & Schuell) containing 0.1 milligrams of fluorogenic substrate were inoculated with 25 microliters of a suspension of Seratia marcescens (ATCC 1343). Cell density of the suspension was adjusted to an optical density of 1.76 at 600 nm as read in a 16 mm diameter tube. As shown in FIG. 6, the plot of fluorescence increase as a function of time observed with L-leucine 7 amido-4-methyl coumarin was nearly linear over the entire ten minute test period. The similar kinetic plot, FIG. 7, obtained with the substrate L-phenylalanine 7 amido-4-methyl coumarin (Sigma) was nearly hyperbolic in shape, with an initial lag phase followed by a more rapid increase in fluorescence. The kinetic curve obtained, FIG. 8, with L alanine 7-amido-4-methyl coumarin was parabolic in shape, with an initial phase of rapid reaction followed by a progressive decrease in rate with increasing time. Thus, different substrate/organism combinations produce rates with different kinetic characteristics. In cases where the kinetics are linear, or close to linear, the rate of reaction can be estimated by a linear regression analysis or from a two-point calculation employing the initial and final measurements of fluorescence. Non linear kinetic data can be treated with higher order regression formulae; data showing an initial lag phase, followed by a period of linear response, followed by a terminal stationary phase sigmoidal response can be analyzed by treating the linear, middle portion of the curve.

EXAMPLE 6

This example demonstrates that various species of microorganisms may be differentiated by differences in the rates at which they hydrolyze various fluorogenic substrates.

Cellulose disks (Cat. No. 740-E, Schleicher & Schuell containing 0.1 mg of fluorogenic substrate per disk were placed in wells of black polystyrene microwell trays and were inoculated with 50 microliters of organism suspension in 0.1 M tris saline buffer, pH 7.8. The optical density of the suspension was adjusted to 1.76 at 600 nm. The substrates tested included 4-methylumbelliferone derivatives of palmitic acid, B-D-glucoside, phosphate and galactoside, plus L-alanine-7-amido 4-methyl coumarin. The organisms tested included Staphylococcus aureus (SA), Pseudomonas aeruginosa (PA), Escherichia coli (EC), Morganella morganii (MM) and Enterobacter aerogenes (EA). The control (C) reactions were performed using inoculation with buffer only. The rates (nanograms liberated fluor/min.) of substrate hydrolysis were determined by reading the fluorescence increase every minute for ten minutes using a Micro-FLUOR ™ reader (Dynatech to yield data values proportional to sample fluorescence and then computing the slope of the linear portion of each kinetic curve by linear regression. The results in Table 5 show the mean rates of hydrolysis plus or minus one standard deviation for each species/substrate combination. Each mean represents the average of 50 rate experiments; five strains per species, 10 samples per strain. Table 5 also includes a differentiation matrix indicating which species pairs are differentiated by each substrate. If the mean rates (+/31 one std. deviation) for two species did not overlap, the rates were significantly different, and the two species were considered differentiated by that substrate. The differentiated pairs are indicated by a (+). Species pairs which were not differentiated by the substrate are indicated by a blank space. All ten species were differentiated by the five substrates using this method.

TABLE 5
DIFFERENTIATION OF SPECIES PAIRS BY RATES OF FLUOROGENIC SUBSTRATE HYDROLYSIS

| Mean | +1STD | −1STD | | SA | PA | EC | MM | EA |
|---|---|---|---|---|---|---|---|---|
| 4-Methylumbelliferyl Phosphate ||||||||| 
| 19.96 | 33.37 | 5.76 | SA | | | | | |
| 1.78 | 3.01 | 0.54 | PA | + | | | | |
| 13.06 | 22.07 | 4.06 | EC | | + | | | |
| 36.16 | 44.27 | 28.04 | MM | | + | + | | |
| 40.20 | 47.69 | 32.69 | EA | | + | | | |
| 0.55 | 0.69 | 0.42 | C | + | | + | + | + |
| 4-Methylumbelliferyl Palmitate ||||||||| 
| 5.06 | 7.25 | 2.87 | SA | | | | | |
| 20.98 | 27.87 | 14.09 | PA | + | | | | |
| 1.14 | 2.61 | −0.32 | EC | | + | | | |
| 2.04 | 3.39 | 0.70 | MM | | + | | | |
| 2.07 | 3.71 | 0.43 | EA | | + | | | |
| 2.70 | 5.91 | −0.52 | C | | + | | | |
| 4-Methylumbelliferyl a-, D-Galactoside ||||||||| 
| 0.03 | 0.20 | −0.12 | SA | | | | | |
| −0.16 | 0.10 | −0.43 | PA | | | | | |
| 2.53 | 4.38 | 0.68 | EC | + | + | | | |
| 0.21 | 0.19 | −0.14 | MM | | | + | | |
| 5.97 | 8.40 | 3.53 | EA | + | + | | + | |
| 0.12 | 0.67 | −0.44 | C | | | + | | + |
| 4-Methylumbelliferyl b-, D-Glucoside ||||||||| 
| 0.29 | 0.98 | −0.40 | SA | | | | | |
| 17.03 | 53.23 | −19.10 | PA | | | | | |
| 0.00 | 0.94 | −0.95 | EC | | | | | |
| 0.56 | 0.94 | −0.83 | MM | | | | | |
| 14.65 | 19.08 | 10.22 | EA | + | | + | + | |
| 0.13 | 1.53 | −1.26 | C | | | | | + |
| L-Alanine-7-Amido-4-Methyl coumarin ||||||||| 
| −0.10 | 0.02 | −0.23 | SA | | | | | |
| 17.54 | 25.02 | 10.06 | PA | + | | | | |
| 35.49 | 47.75 | 23.23 | EC | | | | | |
| 42.49 | 48.78 | 36.19 | M | + | + | | | |
| 50.36 | 61.18 | 39.52 | EA | + | + | | | |
| −0.06 | 0.07 | −0.19 | C | | + | + | + | + |

TABLE 6
SPECIES LIST - BY CLASS

| | ANAEROBES |
|---|---|
| | *Bacteroides fragilis* |
| | *Bacteroides intermedius* |
| | *Peptostreptococcus anaerobius* |
| | *Peptococcus magnus* |
| | *Clostridium perfringens* |
| | GRAM NEGATIVES |
| ENTEROBACTERIACEAE | *Citrobacter freundii* |
| | *Enterobacter aerogenes* |
| | *Enterobacter cloacae* |
| | *Escherichia coli* |
| | *Klebsiella pneumoniae* |
| | *organella morganii* |
| | *Proteus mirabilis* |
| | *Serratia marcescens* |
| NON-FERMENTORS | *Pseudomonas aeruginos* |
| FASTIDIOUS ORGANISMS | *Haemophilus influenzae* |
| | *Haemophilus parainfluenzae* |
| | *Neisseria gonorrhoeae* |
| | GRAM POSITIVES |
| STAPHS | *Staphylococcus aureus* |
| | *Staphylococcus epidermidis* |
| STREPS | *Streptococcus mutans* |
| | *Streptococcus pyogenes* |
| | *Streptococcus agalactiae* B |
| | *Streptococcus faecalis* D |
| | *Streptococcus pneumoniae* |
| YEAST | *Candida albicans* |

EXAMPLE 7

This test was designed to test the interspecies differentiation and the intra-species reproducibility provided by bacterial enzyme rate analysis for 25 of the bacteria most commonly isolated from blood culture bottles. The bacteria tested are listed in Table 6.

Forty-six different fluorogenic substrates were tested. These substrates were fluorescently labeled with either B-methylumbelliferone or 7-amino 4-methyl coumarin. The test measured rates of fluorescence release, as catalyzed by bacterial enzymes generally of the following classes: aminopeptidases, lipases, or glycosidases.

Data were taken every minute over the course of ten minutes by an instrument built expressly for this function. It had a mercury arc lamp as a source, which was internally monitored for normalization. The excitation wavelength used in this test was 365 nanometers. The emission at 440 nanometers was monitored by a gain-proqrammable photomultipler tube. The instrument was controlled by a Ziatech (San Luis Obispo, CA) microprocessor which also controlled X-Y translation of the sample and performed data processing. Sample inoculation was automatic with 25 microliters of bacterial suspension delivered to each substrate site.

Panels were especially manufactured for these tests by the Strouse and Apogee companies (both of Baltimore, MD). Panels were made from flat black polypropylene sheets, each having a length and width of a standard microwell tray. Schleicher & Schuell 740 E absorbent paper (Keene, NH 03431) was punched to a diameter of 6 mm, and attached via adhesive backing (Strouse V-23) to the plastic support. Disk spacing was the same as for wells of a standard microwell tray.

Substrates were prepared by dissolving them in dimethyl sulfoxide (DMSO) and depositing 20 ul of the solutions on the appropriate disks on the panel. The panels were then dried by vacuum evaporation for three hours, packaged in sealed foil pouches with a desiccant, and stored at −20° C. Shortly before testing with inocula the panels were allowed to warm to room temperature. Table 7 lists the substrate solutions used and Table 8 lists the standard solutions.

TABLE 7

SUBSTRATES SOLUTIONS AND ABBREVIATIONS

| SUBSTRATES | CONC. (ug/disk) |
|---|---|
| 4MU-a-D-GALACTOSIDE | 100 |
| 4MU-a-D-GLUCOSIDE | 100 |
| 4MU-a-D-MANNOSIDE | 100 |
| 4MU-a-L-ARABINOSIDE | 100 |
| 4MU-a-L-ARABINOFURANOSIDE | 100 |
| 4MU-B-D-CELLOPYRANOSIDE | 100 |
| 4MU-B-D-FUCOSIDE | 100 |
| 4MU-B-L-FUCOSIDE | 100 |
| 4MU-B-D-GALACTOSIDE | 25 |
| 4MU-B-D-GLUCOSIDE | 25 |
| 4MU-B-D-GLUCURONIDE | 25 |
| 4MU-B-D-MANNOSIDE | 6.25 |
| 4MU-B-D-XYLOSIDE | 025 |
| 4MU-N-ACETYL-B-D-GLUCOSAMINIDE | 100 |
| 4MU-N-ACETYL-B-D-GALACTOSAMINIDE | 100 |
| 4MU-a-D-N-ACETYL-NEURAMINIC ACID | 1.6 |
| 4MU-ACETATE | 2 |
|  | 6.25 |
| 4MU-BUTYRATE | 2.5 |
|  | 25 |
| 4MU-CAPRYLATE | 0.4 |
|  | 6.25 |
| 4MU-ELIADATE | 25 |
| 4MU-P-GUANIDOBENZOATE | 25 |
| 4MU-HEPTANOATE | 6.25 |
|  | 25 |
| 4MU-LAURATE | 10 |
|  | 100 |
| 4MU-NONANOATE | 5 |
|  | 100 |
| 4MU-OLEATE | 8 |
| 4MU-PALMITATE | 25 |
| 4MU-PROPIONATE | 1.56 |
| 4MU-STEARATE | 25 |
| 4MU-SULFATE | 25 |

TABLE 7-continued

SUBSTRATES SOLUTIONS AND ABBREVIATIONS

| SUBSTRATES | CONC. (ug/disk) |
|---|---|
| 4MU-PHOSPHATE | 25 |
| 4MU-PYROPHOSPHATE | 25 |
| 4MU-MYRISTATE | 25 |
| ARGININE-AMC | 6.25 |
| SERINE-AMC | 6.25 |
| GLUTAMATE-AMC | 2.5 |
| GLYCINE-AMC | 0.8 |
| ISOLEUCINE-AMC | 6.25 |
| L-ALANINE-AMC | 6.25 |
|  | 25 |
| LEUCINE-AMC | 6.25 |
| PHENYLALANINE-AMC | 25 |
| PROLINE-AMC | 25 |
| PYROGLUTAMATE-AMC | 5 |
| METHIONINE-AMC | 6.25 |
| TYROSINE-AMC | 100 |
| VALINE-AMC | 6.25 |
| ORNITHINE-AMC | 6.25 |

TABLE 8

STANDARD SOLUTIONS

| SOLUTION | ABBREVIATION | CONCENTRATION (ug/disk) |
|---|---|---|
| B-methylumbelliferone | 4-MU | 0.012 |
|  |  | 0.8 |
| 7-amino-4-methyl coumarin | AMC | 0.012 |
|  |  | 0.8 |

Test inocula were prepared from colonies which were incubated overnight on tryptic soy agar with 5% sheep blood, or on chocolate agar for fastidious organisms. Organism suspensions were prepared to an optical density of 1.76 at 610 nm, in screw cap glass tubes 16 mm×125 mm. The diluent was 0.85% NaCl, 0.02% Triton X100, and 0.1 M Tris which was titrated to pH 8.0. Five strains of each of the species were tested with the exceptions of P. magnus and C. albicans, where only 4 strains were tested, and E. coli, where the five strains were tested in duplicate.

The beam from the instrument's mercury arc lamp was optically split, and output was monitored by a photodetector. Data were normalized internally within the instrument for source variation. Data were further normalized externally by dividing the fluorescence data for the substrates by the fluorescence of the appropriate free fluor standards either B methylumbelliferone or 7-amino 4-methyl coumarin. Enzyme rates are thus expressed as nanograms of free fluor released per minute.

Thresholds for each substrate were determined by examining the spontaneous hydrolysis rates from control panels which were inoculated with buffer only. These were compared to rates from the data base for all organism tested. A threshold rate which would indicate a significant difference from a control rate was determined.

The data generated were analyzed by nearest neighbor analysis utilizing unit sphere projection. This entailed the following steps:

1) A rate was determined based on 1 and 5 minute data points or by using a default rate estimator for readings which exceeded the dynamic range of the instrument.

2) The rate was compared to a threshold selected for each substrate. If the rate was smaller than the threshold then the ratio was set to 1, otherwise the ratio of the rate to the threshold value for that substrate was computed.

3) The log of that ratio was taken.

4) The log ratio value of each of the substrates was squared and then those values were summed.

5) The square root of the sum was then computed (this is the magnitude of the substrate rate vector).

6) The log ratio for each substrate was divided by the magnitude derived in 5 above.

The substrate values were thereby normalized to the unit vector. This method was found to permit direct comparison of inocula of various cell densitie without knowledge of the actual cell densities.

The nearest neighbor for each of the 128 strains tested was computed by taking the absolute difference for each substrate for each species pair in a confusion matrix. The sum of these absolute differences for all substrates within a species pair was determined. The minimum difference between an "unknown" and a "reference" strain determined the nearest neighbor, or best identification of the unknown.

Using this technique, each strain tested identified to another strain of the same species as its nearest neighbor for 95% of the tests. The following species mis-identifications occurred:

| ACTUAL ID | MIS-IDENTIFCATION |
|---|---|
| K. pneumoniae | P. mirabilis |
| H. influenzae | H. parainfluenzae |
| E. aerogenes | K. pneumoniae |
| E. coli | C. freundii |
| E. coli | C. freundii |

However, 95% accuracy is well within the expected performance for commercially available identification test kits.

EXAMPLE 8

Fluorogenic substrates and free fluors may be used to determine enzyme levels of biological samples. The activity of some enzymes has been determined traditionally by testing for acidic and basic by-products of enzyme catalyzed reactions. Fluorescent pH indicators, such B-methylumbelliferone, may be useful for this purpose in properly buffered systems. The fluorescence of B-methylumbelliferone is affected by pH in the range of approximately pH 6.2–8.6. When this change in fluorescence is measured on the fluorescence enhancing supports of the present invention as opposed to in microwells the sensitivity is greatly enhanced.

Figure 9:
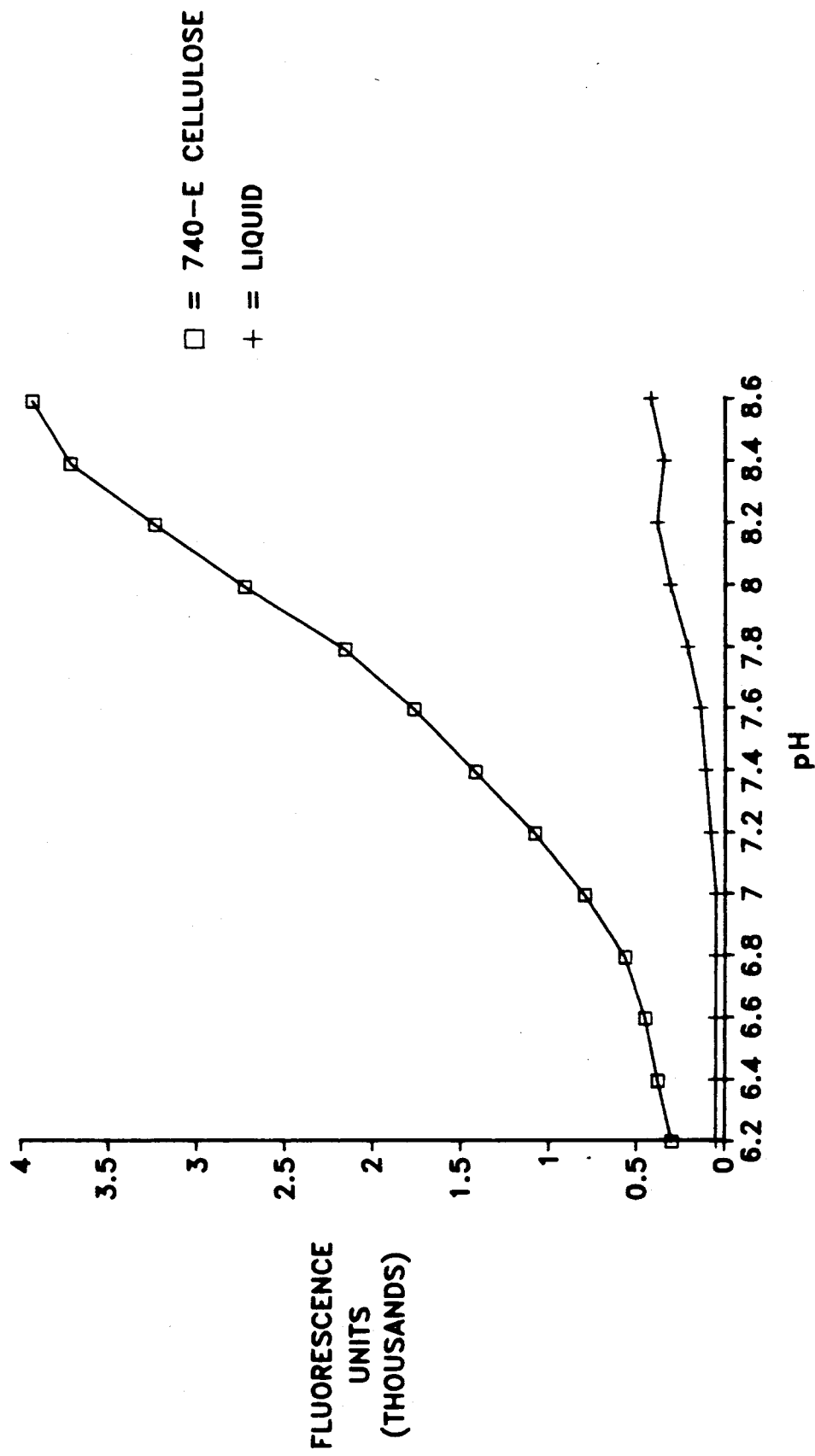
FIG. 9 shows the effect of pH on the fluorescence signal of B-methylumbelliferone (Example 8).

In this example, 500 ng of B-methylumbelliferone dissolved in reagent alcohol was deposited on a 6 mm disk of Schleicher & Schuell 740 E filter paper (Keene, N.H.) and in dry microwells (MicroFluor "B" TM, Dynatech, Chantilly, Va. The solvent was allowed to dry by evaporation. The fluor was reconstituted with 25 microliters of BIS TRIS Propane buffer, the pH of which was adjusted in increments of 0.2 to be between pH 6.2 and 8.6. Fluorescence was read with a fluorometer (Dynatech). As can be seen from the data shown in FIG. 9, the fluorescence on the cellulose support is greatly enhanced over that in the microwells.

Traditional bacterial identification schema employ arrays of biochemical materials which are incubated with an unknown bacterial species. If the bacteria react with a material, the by-product is often basic or acidic. These by-products can be detected with appropriate pH indicators such as phenol red or bromothymol blue. Thus, such reactions are interpreted as being either positive or negative, and bacteria are grouped and speciated by these patterns of positive or negative reactions.

A fluor such as B-methylumbelliferone which is affected by pH when deposited on the kinetics and fluorescence enhancing supports of the present invention can be used to provide bacterial identifications in much less time than conventional testing.

Testing for the presence of urease is common and useful in bacterial identification. If urease is present urea hydrolizes to form ammonia, carbon dioxide and water. In solution the end product is ammonium carbonate which increases the pH of the solution.

The device of the present invention was used to test for the presence of urease. A solution containing urea (10% by weight), B umbelliferone (500 ng) and phosphate buffer (1.25 mM, pH 7.4) was deposited on a cellulose disk (740-E Schleicher & Schuell, Keene, N.H.)and allowed to dry. Thereafter the disks were reconstituted with 25 ul of organism suspensions in normal saline (0.85% NaCl). The organism suspensions were prepared to a density of 2.0 McFarland units. Fluorescence was read immediately following inoculation and again after 15 minutes incubation at room temperature. The increase in fluorescence units observed are reported in Table 10.

TABLE 10

| TEST ORGANISM | INCREASE IN FLUORESCENCE UNITS |
|---|---|
| P. mirabilis (ATCC 2011) | 86 |
| M. morganii (ATCC 434) | 957 |
| Diluent only | 35 |

The M. moganii is a very strong urease producer, and the P. mirabilis tested is a weak urease producer.

EXAMPLE 11

Organisms which express the enzyme beta-lactamase are resistant to penicillins and cephalosporin antibiotics which contain beta-lactam rings that are hydrolized by the enzyme. As shown in below, hydrolysis of the beta lactam ring of the monobasic acid penicillin G yields a dibasic acid.

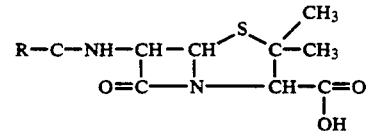

in the presence of Beta-lactamase plus water hydrolyzes to:

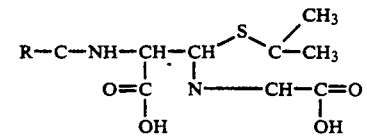

This phenomenon was used to assay for the presence of beta-lactamase using the kinetics and fluorescence device of the present invention. For this experiment cellulose discs were prepared to contain of Penicillin G and 5 ug B-methylumbelliferone which was adjusted to pH 8.0 when in aqueous form. The discs were dried overnight at 35° C.

Organism suspensions were prepared and adjusted to a density of 3.0 McFarland units in 25 mM phosphate buffer which had been titrated to pH 8.0. Aliquots of the suspensions (25 ul) were inoculated onto each disk and an initial fluorescence reading was taken. A final fluorescence reading was taken 15 minutes later. The change in fluorescence signal was determined. The organisms were also tested using a standard beta-lactamase test (Nitrocefin disk, Becton Dickinson Microbiology Systems, Cockeysville, MD). As can be seen from the data reported in Table 11, the organisms which tested positive for beta lactamase in the commercial test showed substantially greater decreases in fluorescence than the organisms which tested negative. Additionally the strain of *B. catarrhalis* tested is known to produce more beta-lactamase than the strain of *S. aureus* tested.

TABLE 11

| STRAIN TESTED | STANDARD TEST | FLUORESCENCE DECREASE | PERCENT CHANGE |
|---|---|---|---|
| *S. edidermidis* ATCC 154 | neg | 255 | 92 |
| *N. meningitidis* ATCC 425 | neg | 337 | 122 |
| *S. aureus* ATCC 29213 | pos | 530 | 192 |
| *B. catarrhalis* ATCC 2907 | pos | 779 | 282 |
| Negative control | N/A | 276 | N/A |

What is claimed is:

1. A kinetics and fluorescence enhancing test device comprising:
   a carrier,
   at least one kinetics and fluorescence enhancing support selected from the group consisting of alpha-cellulose and pH neutralized glass fibers, and
   a dry substance selected from the group consisting of fluorogenic substrates deposited on the support,
   wherein the support has a surface area to void volume ratio of 0.8–80 mm$^2$/0.001cc–0.025cc.

2. The device of claim 1 wherein a plurality of supports are provided.

3. The device of claim 2 wherein at least some supports within the plurality differ from other supports within the plurality in the identify or concentration of the fluorogenic substrate.

4. The device of claim 2 wherein the fluorogenic substrates are selected from the group consisting of derivatives of 4-methylumbelliferone, 7-amino-4-methyl coumarin, B-napthylamine, fluoroscein, and resorufin.

5. The device of claim 2 wherein the fluorogenic substrates are derivatives of coumarin.

6. The device of claim 1 wherein the dry substance is B-methylumbelliferone.

7. The device of claim 1 wherein the dry substance is resorufin.

8. The device of claim 1 wherein the dry substance is flourescein.

9. The device of claim 6 further comprising a non fluorogenic substrate deposited on the support.

10. The device of claim 7 further comprising a non fluorogenic substrate deposited on the support.

11. The device of claim 8 further comprising a non fluorogenic substrate deposited on the support.

12. The device of claim 2 wherein the carrier is microwell plate with a plurality of test wells and the supports are in the test wells.

13. The device of claim 2 wherein the carrier is a planar card and the supports are secured to the card.

14. A method to characterize enzymes present in a fluid sample comprising:
   providing the test device of claim 2;
   adding a fluid sample to each support;
   testing each support to detect fluorescence hydrolysis products to develop a profile of enzyme content in the sample.

15. A method to identify a microorganism in a fluid sample comprising characterizing the enzymes expressed by the microorganism by:
   providing the test device of claim 3;
   adding a portion of the fluid sample to each support;
   testing each support to detect fluorescent hydrolysis products to develop a profile of enzyme content; and
   identifying the microorganism by comparing the profile of enzyme content detected to profiles of enzyme content of reference microorganisms.

* * * * *